United States Patent [19]

Burns

[11] Patent Number: 4,527,561
[45] Date of Patent: Jul. 9, 1985

[54] AUTOMATIC RETRACTABLE LANCET ASSEMBLY

[75] Inventor: James A. Burns, Elizabeth, N.J.

[73] Assignee: Becton, Dickinson and Company, Paramus, N.J.

[21] Appl. No.: 572,336

[22] Filed: Jan. 20, 1984

Related U.S. Application Data

[60] Division of Ser. No. 322,344, Nov. 18, 1981, abandoned, and a continuation-in-part of Ser. No. 246,523, Mar. 23, 1981, Pat. No. 4,388,925.

[51] Int. Cl.³ .............................................. A61B 17/34
[52] U.S. Cl. .............................. 128/314; 128/329 R; 128/637
[58] Field of Search ................ 128/329 R, 314, 315, 128/329 A, 330, 638, 770, 637; 604/156, 157, 136, 137, 46, 47

[56] References Cited

U.S. PATENT DOCUMENTS

| | | | |
|---|---|---|---|
| 55,620 | 6/1866 | Capewell | 128/329 R |
| 1,135,465 | 4/1915 | Pollock | 128/314 |
| 2,531,267 | 11/1950 | Harnisch | 604/136 |
| 3,030,959 | 4/1962 | Grunert | 128/329 R |
| 3,208,452 | 9/1965 | Stern | 128/315 |
| 4,120,303 | 10/1978 | Villa-Massone et al. | 128/330 |
| 4,139,011 | 2/1979 | Benoit et al. | 128/329 R |
| 4,185,635 | 1/1980 | Burford et al. | 128/330 |
| 4,203,446 | 5/1980 | Hofert et al. | 128/329 R |
| 4,442,836 | 4/1984 | Meinecke et al. | 128/314 |

OTHER PUBLICATIONS

Sutor et al., "Bleeding from Standardized Skin Punctures", A.J.C.P., vol. 55, May 1971.

Primary Examiner—Michael H. Thaler
Attorney, Agent, or Firm—Robert P. Grindle

[57] ABSTRACT

An automatic retractable lancet assembly includes a housing with a sharp-pointed lancet movably mounted therein. A depressible plunger and slide mechanism actuates the movement of the lancet outwardly from the housing. After this outward movement is completed, the actuator elements become dissociated from further movement of the lancet. Subsequently, the lancet is automatically retracted back inside the housing by virtue of a spring element.

2 Claims, 28 Drawing Figures

AUTOMATIC RETRACTABLE LANCET ASSEMBLY

This is a division of application Ser. No. 322,344, filed Nov. 18, 1981, now abandoned, and a continuation-in-part application of application Ser. No. 246,523, filed Mar. 23, 1981, U.S. Pat. No. 4,388,925.

BACKGROUND OF THE INVENTION

1. Field of the Invention

The present invention relates to a lancet assembly, and more particularly, concerns an automatic retractable lancet assembly useful in penetrating the skin of a patient.

2. Description of the Prior Art

Sharp-pointed lancets are employed to make a quick puncture or penetration of the patient's skin in order to provide a small outflow of blood. Various tests may be employed with only small amounts of blood so that the blood flowing from a finger prick is normally sufficient. However, due to the sensitive nerve endings in the finger tip area, this procedure could induce a significant amount of pain in the patient even though the skin puncture produces minimal cutting. In order to minimize potential pain, it is desirable to make the thrust of the lancet through the patient's skin rapidly.

Spring-loaded lancets of different types and forms have been well known and are typified, for example, by U.S. Pat. Nos. 55,620; 1,135,465; 3,030,959; 4,139,011; 4,203,446; 4,230,118; Swedish Pat. No. 124247 and Sutor, A. H., et al., "Bleeding From Standardized Skin Punctures: Automated Technique for Recording Time, Intensity and Pattern of Bleeding," A. J. C. P., Volume 55, May 1971.

U.S. Pat. No. 4,203,446, above, is significant in that it teaches the puncture of the skin of a patient with a lancet which is retracted back into the device after piercing the patient's skin. In the patented device, the downward motion of the lancet is initiated by the impact of a spring-loaded hammer, and as this motion continues, the spring potential decreases. At the time of impact, the return spring begins to compress and increase potential energy. When the potential energy in the return spring under compression exceeds the potential energy in the driving spring, compression of the return spring ends and decompression begins. This, then, reverses the motion of the lancet. However, impact is necessary to compress the return spring and increase its potential energy rapidly. Without the impact force, the spring forces would approach equilibrium and then there would be no reverse motion in order to retract the lancet out of the patient's skin. Furthermore, since spring potential is critical in this patented device, a conical spring is relied upon to overcome recoil due to the surge of the larger return spring. Despite the foregoing inventions, improvements in this field of lancets are still being sought.

SUMMARY OF THE INVENTION

An automatic retractable lancet assembly of the present invention comprises a housing with a sharp-pointed lancet movably mounted therein. Actuating means moves the lancet outwardly from the housing and thereafter becomes dissociated from further movement of the lancet. Subsequent to this outward movement of the lancet, operable means is provided for automatically retracting the lancet back inside the housing.

In the preferred embodiment of the present invention, the housing includes an aperture with the lancet mounted in the housing so that its point lies adjacent the interior side of the aperture. A depressible plunger is movably mounted in the housing in the end thereof opposite from the lancet. Also mounted inside the housing is a first spring in a compressed condition adapted to decompress upon the plunger being depressed into the housing. This causes the movement of the lancet outward of the aperture for penetration of the skin of a patient. The first spring is adapted to become dissociated from the lancet after the lancet completes its outward movement. A second spring is mounted inside the housing in a substantially decompressed condition before the plunger is depressed. This second spring is adapted to become compressed during outward movement of the lancet. Furthermore, the second spring is adapted to decompress when the first spring becomes dissociated from the lancet. This causes the lancet to be automatically retracted back inside the housing.

In accordance with the principles of the present invention, the desired functions are achieved by virtue of structure which is notably different from the structure of prior art lancet assemblies. In particular, and in the preferable embodiment, two springs are employed to complete the intended purpose of the lancet. The first spring serves as a driving spring to rapidly thrust the lancet outwardly for penetration of the patient's skin. At this time, this driving spring becomes dissociated from movement of the lancet. The second spring serves as a return spring, operable after the driving spring has become so dissociated. Therefore, when the second or return spring automatically retracts the lancet back into the housing, there is no opposing spring force, such as found in U.S. Pat. No. 4,203,446. Thus, in the present invention, the various spring potential energies do not have to balance as in the aforementioned patented invention. The return spring of the present invention only has to be sufficiently strong to retract the lancet inwardly. Therefore, considerations of balancing spring forces, as in the previous inventions, have been obviated by the structure of the present invention. This allows the design of the present invention to include a greater liberality as far as spring sizes and strengths are concerned. Advantageously, the present invention provides a quick thrust of the lancet outwardly to penetrate the skin of the patient, and then automatically retracts the lancet from the patient's skin so that dwell time therein is minimized. It is intended that this embodiment of the present invention can be economically fabricated so that it can be discarded after single use in disposable fashion.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figures 1, 3, 4, 9:
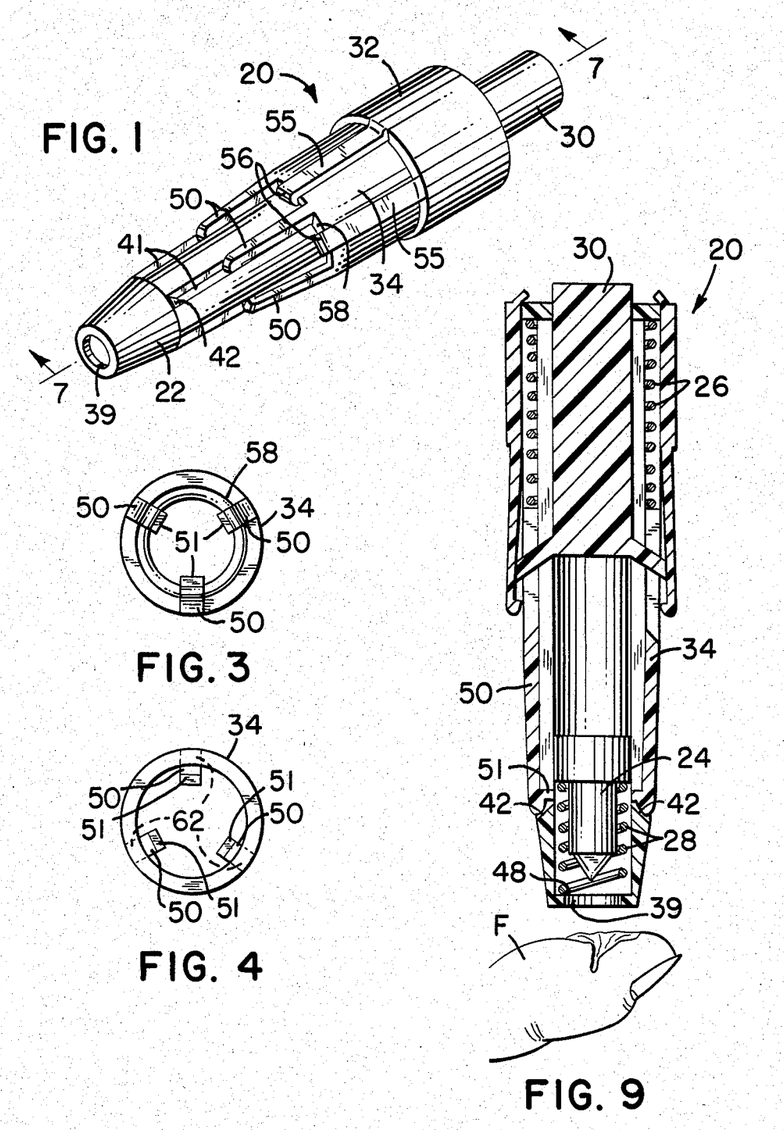
FIG. 1 is a perspective view illustrating the preferred embodiment of the automatic retractable lancet assembly of the present invention.
FIG. 3 is an enlarged end view of the slidable sleeve element taken along line 3—3 of FIG. 2.
FIG. 4 is an enlarged end view of the slidable sleeve element taken along line 4—4 of FIG. 2.
FIG. 9 is a cross-sectional view of the lancet assembly of FIGS. 7 and 8 illustrating the next sequential operative step after the lancet has been automatically retracted back into the assembly after the finger of the patient has been penetrated.
Figure 2:
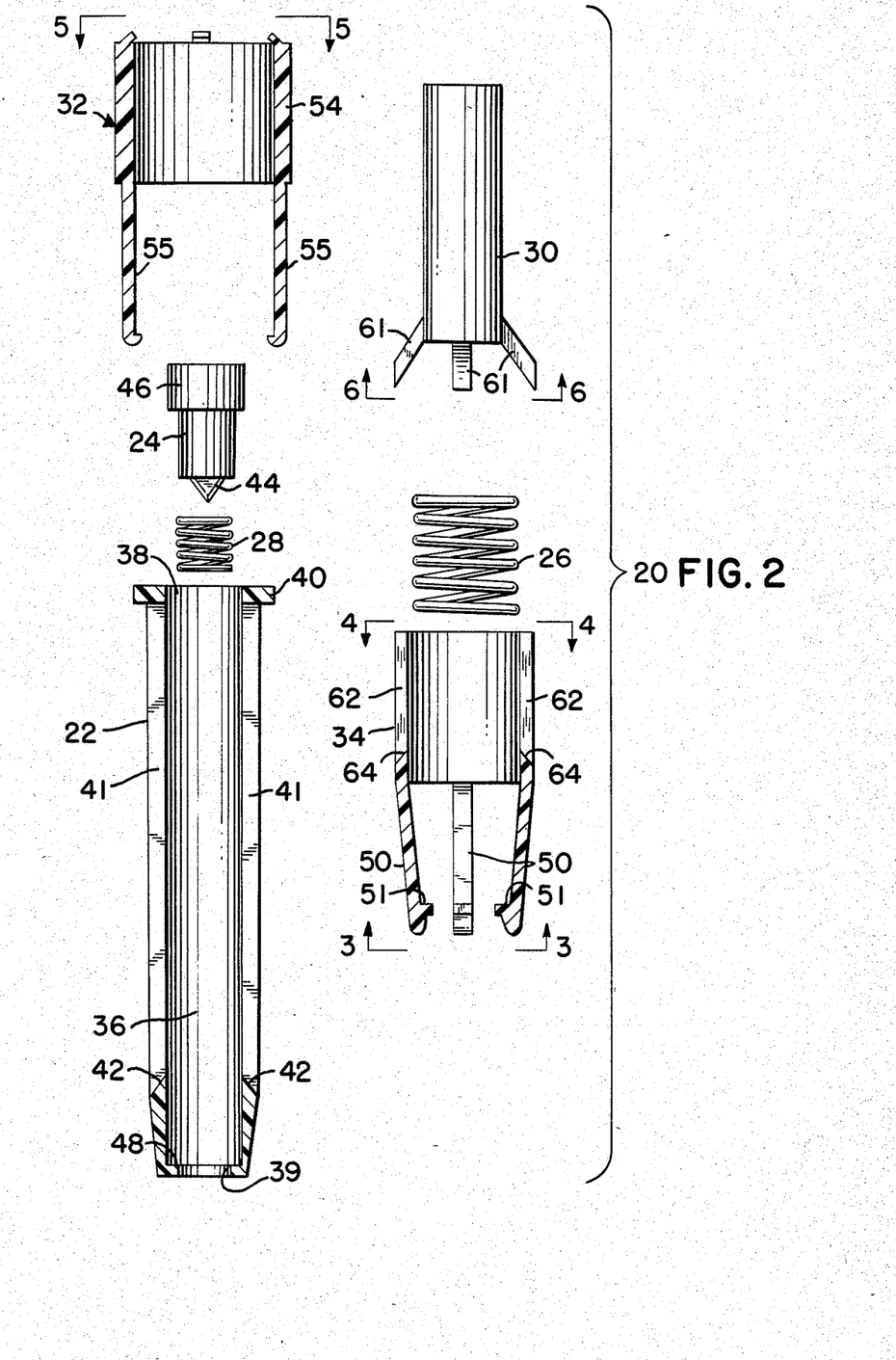
FIG. 2 is an exploded assembly plan view of the elements of the automatic retractable lancet assembly of FIG. 1.

Referring to the drawings, and FIGS. 1 and 2 in particular, there is illustrated a preferred embodiment of an automatic retractable lancet assembly 20. As more clearly seen in FIG. 2, taken in conjunction with FIG. 1, the basic components of lancet assembly 20 are the following: a housing 22, a lancet 24, a first spring 26, a second spring 28, a depressible plunger 30, a skirt 32 and a slidable sleeve 34. In this embodiment being described, all of the aforementioned elements are preferably cylindrically shaped and designed for coaxial arrangement with each other as described below.

More specifically, housing 22 is an elongate hollow tube having a passageway 36 therethrough terminating in an opening 38 at its proximal end and an aperture 39 at its distal end. An annular flange 40 surrounds opening 38 for structural purposes in maintaining the elements together when assembled. In this particular embodiment, there are three longitudinal slots 41 (only two being shown in FIG. 2 since they are spaced approximately 120° apart) through the peripheral wall of housing 22. These slots terminate toward the distal end of the housing at slanted, inclined surfaces 42.

Figure 7:
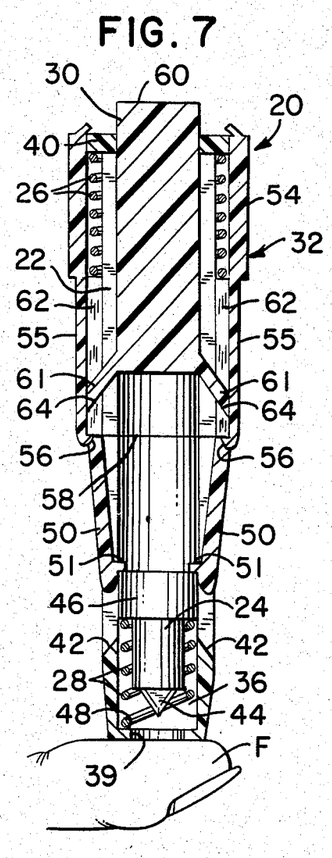
FIG. 7 is a cross-sectional view of the automatic retractable lancet assembly taken along line 7—7 of FIG. 1 illustrated in position in conjunction with a finger of a patient.

Lancet 24 includes a sharp point 44 extending from a slidable piston 46. As more clearly seen in FIG. 7 which represents the instant invention in the assembled condition before use, lancet 24 is slidably positioned inside passageway 36. The diameter of piston 46 is designed to slide within the inside diameter of passageway 36 of housing 22. Sharp point 44 faces toward aperture 39 and is maintained inside the housing adjacent the interior side of aperture 39. Second spring 28 is provided to maintain the lancet in this position. Spring 28 is basically a coil spring which fits around the sharp point of the lancet so that piston 46 rests upon this spring. An inwardly projecting lip 48 at the distal end of the housing cooperates to hold the spring inside the housing. In this position as seen in FIG. 7, which represents the lancet assembly before use, spring 28 is in a substantially decompressed condition.

Slidable sleeve 34 is adapted to slide over housing 22 in coaxial fashion. This sleeve includes three flexible legs 50 spaced approximately 120° apart, as illustrated in FIGS. 3 and 4, and adapted to correspond to slots 41 of the housing. Each flexible leg includes an inwardly projecting foot 51 which projects through corresponding slot 41 in the housing. As seen in FIG. 7, feet 51 engage the top of piston 46 of the lancet. This engagement helps maintain the lancet in a relatively immobile position in the pre-use condition.

Figure 5:
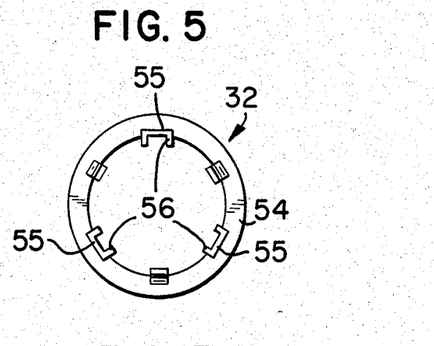
FIG. 5 is an enlarged end view of the skirt element of the preferred invention taken along line 5—5 of FIG. 2.

Skirt 32, also preferably cylindrically shaped, includes an upper portion 54 which is sized to snugly fit around flange 40 of the housing. The bottom portion of skirt 32 includes three flexible arms 55 extending downwardly, as seen in FIG. 5. Each arm 55 has at its distal end a hook 56 projecting inwardly. In the assembled condition as seen in FIG. 7, skirt 32 is oriented so that arms 55 are peripherally offset from legs 50 of the slidable sleeve. In this manner, hooks 56 fit between legs 50 and engage the flat surfaces 58 on the sleeve between the legs. This immobilizes slidable sleeve in a relatively fixed condition before the lancet assembly is used. In this condition, first spring 26 is compressed between the proximal end of slidable sleeve 22 and flange 40 of the housing. First spring 26 is essentially similar to second spring 28 inasmuch as it is a coil spring. This first spring is, however, larger in diameter and should be designed with a larger spring force inasmuch as it is in the driving spring for rapidly thrusting the lancet through the skin of the patient. With the hooks at the end of the skirt engaging the flat surfaces of the slidable sleeve, first spring 26 is effectively maintained in the compressed condition before use of this lancet assembly, as more clearly seen by referring to FIG. 7.

Figure 6:
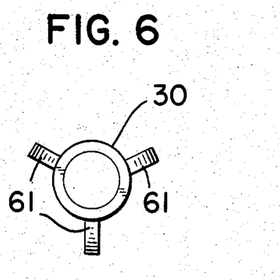
FIG. 6 is an enlarged end view of the depressible plunger element of the preferred invention taken along line 6—6 of FIG. 2.

Depressible plunger 30 is preferably a cylindrically shaped plug with a flat push-button surface 60 at its proximal end. Depending from the distal end of plunger 30 are three equally spaced flexible arms 61, as illustrated in FIG. 6. Plunger 30 is slidably positioned inside housing 22 in the end opposite from the lancet so that flexible arms 61 project through slots 41 running along the longitudinal axis of the housing. In addition, flexible arms 61 also project through slots 62 which run longitudinally in the proximal portion of slidable sleeve 34 as illustrated in FIG. 4. Slots 62 are oriented to correspond with the orientation of slots 41 in the housing. Slots 62 terminate distally in slanted, inclined surfaces 64 which can be seen in FIG. 7. In the loaded condition before use, flexible arms 61 of the plunger may either contact inclined surfaces 64 or be slightly spaced therefrom. In either case, the flexible arms of the plunger are adapted to engage the inclined surfaces on the slidable sleeve when the plunger is downwardly depressed. FIGS. 1 and 7 illustrate the automatic retractable lancet assembly of the present invention in the loaded condition as it would appear before use. In FIG. 7, a finger F of the patient is positioned adjacent the distal end of the assembly just before use so that the finger covers aperture 39. The operation of this lancet assembly, illustrating penetration of the skin of the finger and then automatic retraction of the lancet is seen in FIGS. 8 and 9.

Figure 8:
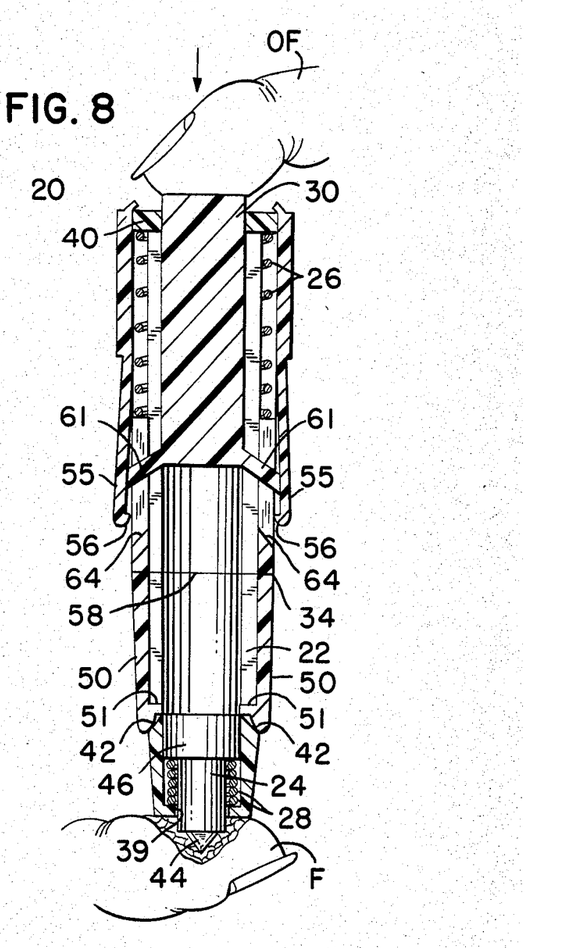
FIG. 8 is a cross-sectional view of the lancet assembly of FIG. 7 illustrating the sequential operation of the assembly to penetrate the finger of the patient.

Turning to FIG. 8, in particular, lancet assembly 20 is shown in position on top of finger F of a patient, while the finger of the operation OF is illustrated pushing downwardly on depressible plunger 30. This downward movement causes flexible arms 61 of the plunger to engage inclined surfaces 64 on the slidable sleeve. Inasmuch as hooks 56 of the skirt maintain the slidable sleeve in a fixed position, contact of flexible arms 61 against inclined surfaces 64 causes the arms to flex outwardly. This outward flexure causes contact with flexible arms 55 of the skirt. In turn, flexible arms 55 flex outwardly a sufficient amount so that hooks 56, at the end of flexible arms 55, become disengaged from flat surfaces 58 on the slidable sleeve. Once this disengagement occurs, there is no force tending to compress spring 26 into the compressed condition. As a result, with the restraining force removed, the spring is released causing an expansion of the spring. This expansion causes sleeve 34 to move distally within housing 22 in a rapid thrusting movement. Inasmuch as feet 51 at the distal end of the sleeve are in engagement with the piston portion of lancet 24, the lancet also moves distally. Sharp point 44 moves rapidly out of aperture 39 and penetrates finger F positioned just under the aperture. While this is occurring, it is noted that the distal movement of lancet 24 has caused second spring 28 to become compressed. This compression is a direct result of the energy transmitted to slidable sleeve 34 by the release of first spring 26. In order to assure proper compression of second spring 28, it is desirable that the first or driving spring have a higher spring constant than the second or return spring.

In addition to causing downward movement of lancet 24 and compression of second spring 28, the downward or distal movement of slidable sleeve 34 causes flexible legs 50 to engage inclined surfaces 42 on housing 22. As a result, the downward movement of flexible legs 50 against inclined surfaces 42 causes these flexible legs to flex outwardly. As a consequence, inwardly projecting feet 51 become disengaged from the piston portion of lancet 24. This condition is more clearly seen by referring to FIG. 9. Inasmuch as feet 51 serve as the restraining force against second spring 28 when compressed, the disengagement of these feet from the lancet effects a release of this spring. This in turn causes an expansion of spring 28 thereby rapidly retracting lancet 24 back inside the housing. It is noted that when spring 28 expands its entire energy is transmitted only to lancet 24 to effect its retraction back inside the housing. With feet 51 disengaged, slidable sleeve 34 also becomes dissociated from the retraction movement of the lancet caused by expansion of second spring 28. Therefore, when second spring 28 expands, it is not working against the decompressed state of first spring 26 since the disenagagement of feet 51 dissociate the entire slidable sleeve and first spring 26 from the retraction movement of the lancet and the decompression of second spring 28. Accordingly, with a low amount of energy required to retract the lancet back inside the housing, second spring 28 can be a small lightweight and inexpensive spring. It is appreciated that the structure of the present lancet assembly causes not only the rapid thrusting movement of the lancet to penetrate the skin of the patient, but also effects the automatic retraction of the lancet back inside the housing of the assembly. Thus, downward depression of plunger 30 is the stimulus for both outward release and inward retraction of the lancet. Insofar as a preferred embodiment of the present invention is intended to be disposable, the housing, slidable sleeve, flexible skirt and depressible plunger can be fabricated of inexpensive plastic materials. On the other hand, lightweight metals can be employed for the lancet and the two springs described above.

Turning now to the embodiment illustrated in FIGS. 10–14, lancet assembly 70 is comprised of a relatively flat housing 71 which may be fabricated in two parts for ready assembly. Inside housing 71 is a first block 72 to which two springs are connected: a first preferably flat coil spring 74 and a second also preferably flat coil spring 75. Both of the coil springs preferably have a plurality of compressible folds lying substantially along a flat plane inside housing 71, although spring 74 preferably has a higher spring constant than spring 75. Connected to the other end of flat spring 75 is a lancet block 76. At the distal end of lancet block 76 is a sharp pointed lancet 78. It is preferred that springs 74 and 75, block 72 and lancet block 76 be fabricated as an integral, unitary structure. For example, and while other materials may be used, the composite structure of springs, and two blocks, may be made of plastic material with the flat springs being very thin and thus highly resilient in nature. Lancet 78 at the distal end of lancet block 76 is preferably made of metal to facilitate penetration of the skin of a patient.

Figures 10, 11, 12:
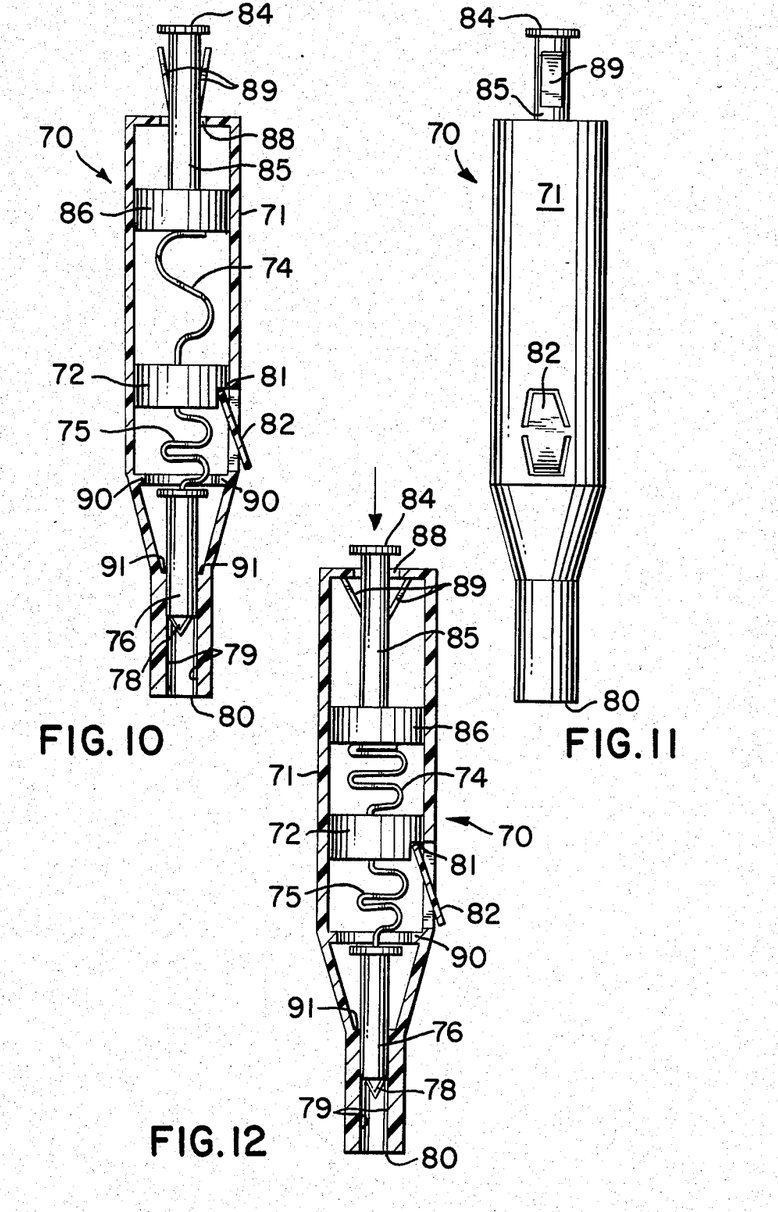
FIG. 10 is a cross-sectional view of an alternate embodiment of the lancet assembly of the present invention illustrating the assembly in a pre-loaded condition.
FIG. 11 is a side view of the lancet assembly of FIG. 10.
FIG. 12 is a cross-sectional view of the lancet assembly of FIG. 10 illustrated in the loaded condition for use.

FIG. 10 depicts lancet assembly 70 in a relaxed, or preloaded condition. In FIG. 10, there is no compression on either of the springs. Lancet block 76 is partially positioned in bore 79 at the distal end of housing 71. Bore 79 terminates in an aperture 80 at the distal end of the housing. Block 72 is adapted to slide inside the interior of housing 71 and is dimensioned accordingly. Block 72 includes a notch 81 partially cut from its body so that a depressible button 82 may be engaged therein. Button 82 is preferably a cut-out portion of housing 71 adapted to pivot for example, on a living hinge (not shown) formed in housing 71.

Turning now to FIG. 12, lancet assembly 70 is loaded by pressing inwardly on flange 84 at the top of a slidable plunger 85. Connected to plunger 85 inside housing 71 is a slidable piston 86. It can be seen in FIG. 12 that when plunger 85 is depressed inwardly, piston 86 compresses spring 74. Block 72 remains stationary due to the fact that depressible button 82 is engaged in slot 81. Plunger 85 is depressed through opening 88 in the top of the housing so that the pair of resilient arms 89 also passes through opening 88. Once the arms are inside the interior of the housing, their resilient nature causes them to resiliently deflect outwardly beyond the diameter of opening 88. Therefore, once plunger 85 is depressed to load the lancet assembly, it cannot be readily reloaded, thereby preventing inadvertent reuse. This feature contributes to the disposable nature of the lancet assembly being discussed.

Figures 13, 14, 16:
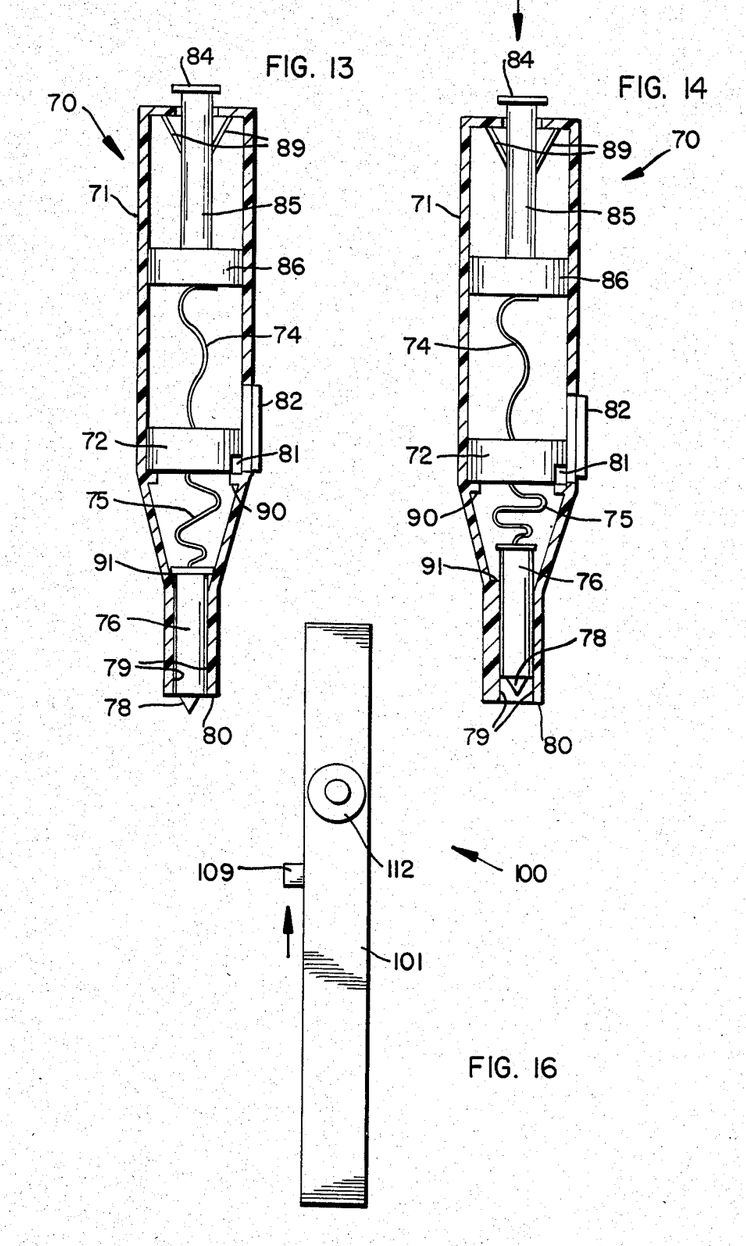
FIG. 13 is a cross-sectional view of the lancet assembly of FIG. 10 illustrating the assembly after it has been fired with the lancet point in position to penetrate the skin of a patient.
FIG. 14 is a cross-sectional view of the lancet assembly of FIG. 10 illustrating the lancet retracted back inside the assembly after use.
FIG. 16 is a side view of the lancet assembly of FIG. 15.

In the loaded condition for firing, spring 74 is under compression, whereas spring 75 remains in the relaxed condition. Referring now to FIG. 13, depressible button 82 is pushed at its lower end (as indicated by the arrow) so that the button becomes disengaged from slot 81 in block 72. This immediately releases the compression on spring 74 and causes block 72 to move distally in the direction toward aperture 80. However, a pair of abutment stops 90 inside housing 71 limits the travel of block 72 after the tension in spring 74 has been released. When block 72 strikes stops 90, the weight of lancet block 76 causes spring 75 to stretch and become biased due to its resilient nature. When this occurs, lancet block 76 slides through bore 79 until lancet 78 emerges outward of aperture 80. A shoulder 91 inside the housing also limits the travel of lancet block 76 through bore 79 so that the emergence of lancet 78 can be controlled. Penetration of the skin of a patient would occur at this step of the utilization of lancet assembly 70.

The occurrence depicted in FIG. 13, it is understood, is only momentary due to the characteristics of spring 75. As illustrated in FIG. 14, spring 75 has returned to its normal relaxed condition, at the same time retracting lancet block 76, with lancet 78, back inside housing 71. It is understood that the retraction mechanism of spring 75 is independent of any action of spring 74. This is due to the fact that once spring 74 is relaxed after being compressed, it is no longer associated with movement of lancet 78. Therefore, when spring 75 returns back to its relaxed condition it is not balancing any spring force remaining in spring 74, but is merely acting independently. The action of spring 75 to return to its relaxed condition, therefore automatically retracts the lancet back inside the housing. The entire sequence to release the lancet and retract same occurs very quickly so as to minimize trauma to the patient. It can be seen by referring to FIG. 14, that once the lancet is retracted back inside the housing, the assembly cannot be reused and is therefore ready to be disposed.

While not shown in the drawings, the embodiment of FIG. 10 may be prepackaged in the loaded condition, i.e., spring 74 may be assembled into housing 71 so that it is already compressed and under tension. This would, of course, eliminate the need for the loading mechanism such as depressible plunger 85. The remaining elements and features of a pre-loaded lancet assembly could be essentially the same as those elements and features previously described.

Figure 15:
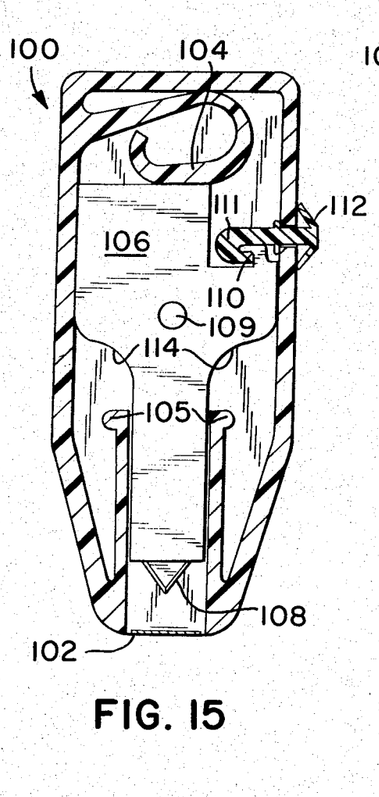
FIG. 15 is a cross-sectional view of another alternate embodiment of the lancet assembly of the present invention illustrating the assembly in a loaded position before use.

Another embodiment of a lancet assembly employing the principles of the present invention is illustrated in FIGS. 15–18. Referring to FIGS. 15 and 16, in particular, lancet assembly 100 includes a housing preferably of a generally flat nature which may be formed in two separable pieces for ready assembly of the components therein. Housing 101 includes an aperture 102 in one end thereof. It is preferred that housing 101 be formed with a number of integral resilient spring members. In particular, a coiled flat spring 104 is formed inside one end of housing 101. At the other end of housing 101, a pair of leaf springs 105 extend inwardly from aperture 102. The coiled and leaf springs, along with the housing, are preferably formed of plastic material so that they may be readily molded. The thickness and shape of the aforementioned springs is designed to impart resiliency thereto.

Figure 17:
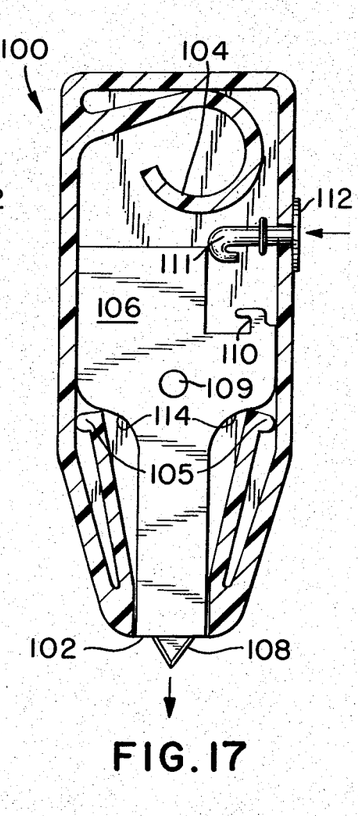
FIG. 17 is a cross-sectional view of the lancet assembly of FIG. 15 illustrating the assembly after it has been fired with the lancet point in position for penetration of the skin of a patient.
Figure 18:
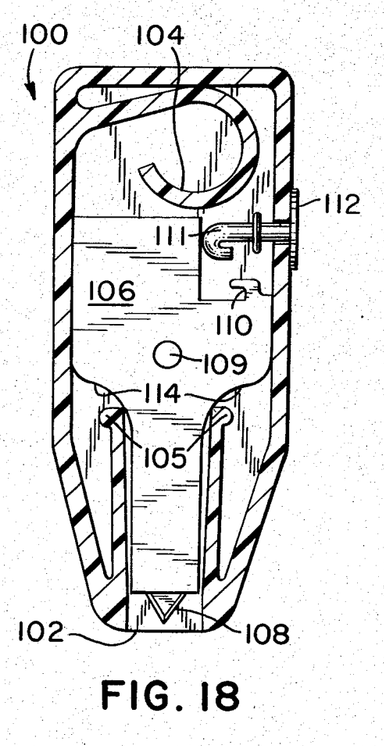
FIG. 18 is a cross-sectional view of the lancet assembly of FIG. 15 illustrating the lancet retracted back inside the assembly after it has been used.

Positioned inside housing 101 is a slidable plunger 106. The upper portion of plunger 106 is sized to slidably fit inside housing 101, whereas the lower portion of plunger 106 is dimensioned to slidably fit between leaf springs 105, which lie substantially parallel to the axis of movement of the plunger. At the distal end of plunger 106 is mounted a sharp pointed lancet 108. A post 109 extends outwardly from the flat surface of housing 101 so that plunger 106 can be loaded for firing, if the lancet assembly is assembled with the internal springs in a relaxed condition. To load the lancet assembly, the user pushes upwardly on post 109 until an undercut notch 110 mates with a hook 111 extending through the side wall of housing 101. When notch 110 and hook 111 are mated, the upper portion of plunger 106 compresses coiled flat spring 104 and places it in tension. At this time, lancet 108 lies adjacent the interior side of aperture 102. To fire lancet assembly 100, the user pushes inwardly on button 112 which is connected to hook 111. Inward movement of hook 111 causes it to become disengaged from notch 110. Due to the tension of coil spring 104 which is released, plunger 106 is rapidly urged in the direction toward aperture 102. The rapid movement of plunger 106 causes lancet 108 to emerge outward of aperture 102. At the same time, inclined surfaces 114 on plunger 106 engage the upper surfaces of leaf springs 105. As can be seen in FIG. 17, such contact by the plunger causes leaf springs 105 to deflect outwardly at the same time lancet 108 emerges from aperture 102. In this regard, deflection of leaf springs 105 momentarily biases them under tension. This tension causes leaf springs 105 to return back to their original, relaxed condition. This, in turn, pushes plunger 106, with lancet thereon, back inside housing 101. This sequential step is illustrated in FIG. 18. It can be seen that leaf springs 105 have returned to their relaxed, normal condition thereby automatically retracting lancet 108 back inside housing 101. As in the previously described embodiments, the action of the leaf springs to retract the lancet back inside the housing takes place independently of coil spring 104. It can be seen in both FIGS. 17 and 18, that the relaxation of the tension from coil spring not only causes the plunger to slide toward the aperture, but also completely disengages the plunger from the flat coiled spring. Therefore, all movement of the plunger back inside the housing after the lancet penetrates the skin of the patient is caused solely by leaf springs 105. There is, thus, no balancing of spring forces required by the structure of this embodiment of the lancet assembly.

Figure 19:
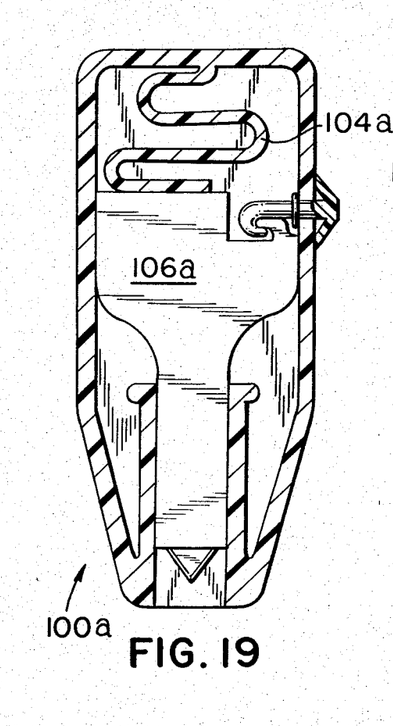
FIG. 19 is a cross-sectional view of another alternative embodiment of the lancet assembly of the present invention illustrating an alternative spring construction to the embodiment of FIG. 15.

The embodiment of FIGS. 15–18 may be slightly modified as illustrated in FIG. 19. Lancet assembly 100a has a coiled flat spring including a plurality of folds therein. The spring constant of the coiled flat spring can thus be modified according to the number of folds formed therein. All other elements of lancet assembly 100a are substantially as described above with respect to FIGS. 15–18.

Figure 20:
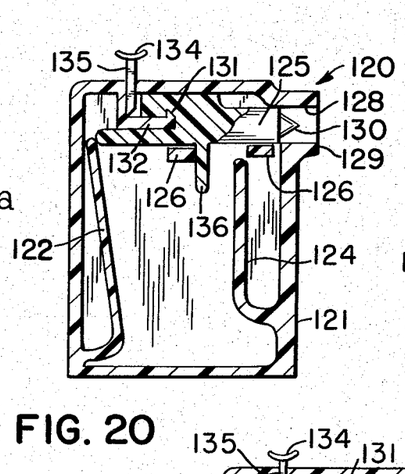
FIG. 20 is a cross-sectional view of still another alternative embodiment of the lancet assembly of the present invention illustrating the assembly in a loaded condition for use.
Figure 21:
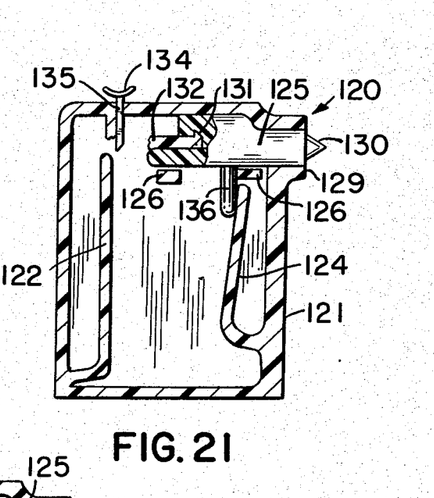
FIG. 21 is a cross-sectional view of the lancet assembly of FIG. 20 illustrating the assembly after it has been fired with the lancet point in position for penetration of the skin of a patient.
Figure 22:
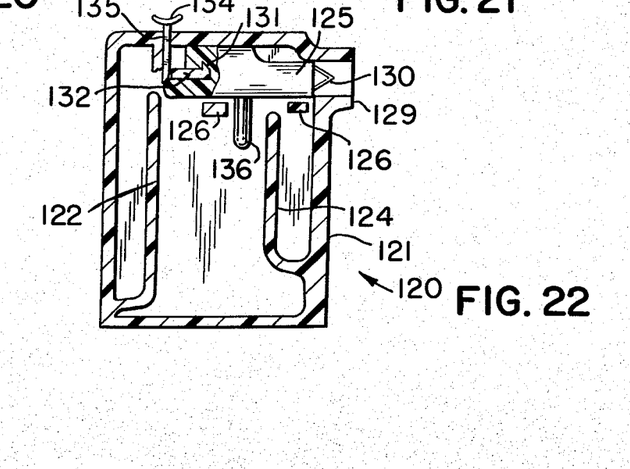
FIG. 22 is a cross-sectional view of the lancet assembly of FIG. 20 illustrating the lancet retracted back inside the assembly after use.
Figure 23:
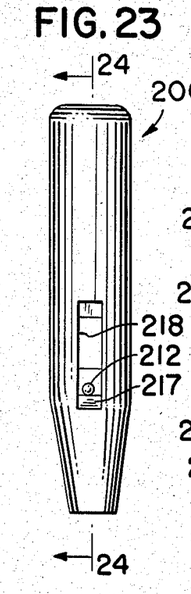
FIG. 23 is a side view of another alternative embodiment of the lancet assembly of the present invention.
Figure 24:
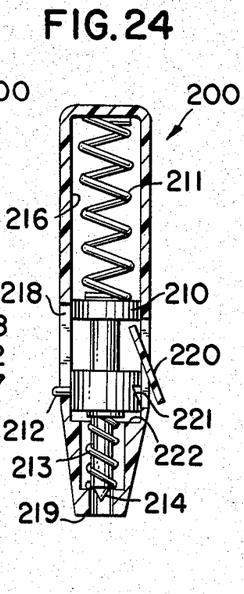
FIG. 24 is a cross-sectional view taken along line 24—24 of FIG. 23 illustrated in a pre-loaded condition.

Instead of the coiled springs as described in the two previous embodiments, a different spring arrangement may be utilized as illustrated in the embodiment of FIGS. 20–22. As seen in FIG. 20, lancet assembly 120 includes a housing 121 which is preferably generally flat and may be comprised of two or more portions for ready assembly. It is preferred that lancet assembly 120 be fabricated with two integrally formed leaf springs, 122 and 124. These leaf springs are desirably connected to the housing so that they extend over a substantial length inside the housing to assure that sufficient resiliency is provided. A plunger 125 is mounted inside housing 121 on one or more tracks 126. Further, plunger 125 has its distal end slidably positioned in a bore 128 extending through housing 121. Bore 128 terminates in an aperture 129. At the distal end of plunger 125 a sharp pointed lancet 130 is mounted.

Plunger 125 is formed with an undercut notch 131 which is adapted to mate with a preferably frangible hook 132 depending from a wall of housing 121. A slidable button is mounted adjacent hook 132 and preferably includes a sharp pointed slidable rod 135 directed toward the bend in hook 132. In addition, plunger 125 includes a downwardly depending flange 136 which is adapted to contact leaf spring 124 as hereinafter described. In the loaded condition for firing, plunger 125 is retained in position by the mating of the previously described hook and notch in a latched arrangement. In this instance, as seen in FIG. 20, leaf spring 122 engages the proximal end of the plunger and is placed under tension. No contact is being made at this time with leaf spring 124.

To use lancet assembly 120, the operator presses inwardly on button 134 so that sharp pointed rod 135 readily fractures hook 132 due to its frangible nature. This causes a release of the tension on leaf spring 122 which rapidly returns to its normal, relaxed position as seen in FIG. 21. At the same time, plunger 125 is urged rapidly in the direction toward aperture 129 until lancet 130 emerges therefrom. Tracks 126 may be positioned to control the distance which lancet 130 travels outward of aperture 129.

By the time the lancet extends out of the aperture, downwardly depending flange 136 on the plunger has come in contact with leaf spring 124 causing the leaf spring to deflect and be placed under tension. As in the previously described embodiments, the bias of the leaf spring 124 is momentary since it rapidly returns back to its normal, relaxed position as seen in FIG. 22. Return of leaf spring 124 to its normal position causes lancet 130 to be automatically retracted back inside housing 121. Retraction of lancet 130 back inside the housing is done independently by leaf spring 124. Inasmuch as leaf spring 122 has become disengaged from contact with plunger 125 after its tension was released, it is only the action of leaf spring 124 which causes the retraction of the lancet back inside the assembly. Therefore, there is no balancing of spring forces against each other in the firing of the lancet for penetration of the skin of a patient and its automatic retraction back inside the assembly.

Referring now to the embodiment illustrated in FIGS. 23–28, assemby 200 comprises a lancet holder 210 with a projecting lift-pin 212, main spring 211, retraction spring 213 and lancet 214. This configuration is more clearly seen by referring specifically to FIGS. 23 and 24. Lancet holder 210 is designed to travel in a housing 215 along sides 216 and is held in position by lift-pin 212 bearing on edge 217 of housing slot 218. Main spring 211 and the significantly lighter and smaller retraction spring 213 are in the normal or relaxed state. Lancet 214 is held in position interiorly of aperture 219.

Figure 25:
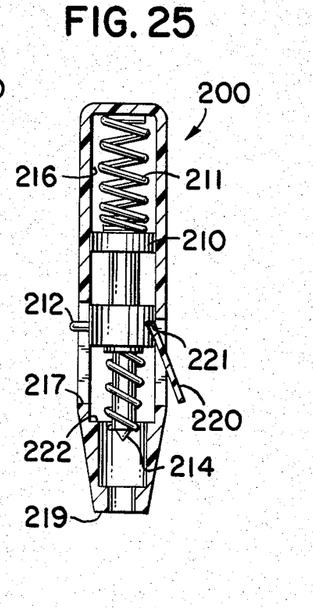
FIG. 25 is a cross-sectional view of the lancet assembly of FIG. 23 illustrating the assembly in a loaded position before use.

Turning to FIG. 25, assembly 200 is illustrated in a loaded condition. Lancet holder 210 has been raised upwardly on sides 216 by the lift-pin 211 and is held in the position shown by latch 220 bearing against notch 221 of the lancet holder. Latch 220 is preferably an integral hinge that is molded as part of housing 215. Main spring 211 is compressed and lancet 214 has been moved to a new upward position from aperture 219. Retraction spring 213 remains in the normal or uncompressed condition.

Figure 26:
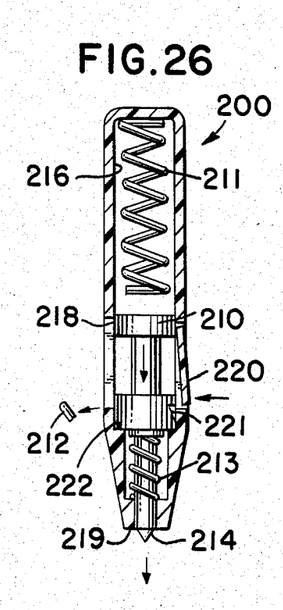
FIG. 26 is a cross-sectional view of the lancet assembly of FIG. 23 illustrating the assembly after it has been fired with the lancet point in position for penetration of the skin of a patient.

As seen in FIG. 26, latch 220 has been pushed in the direction of the arrow to release lancet holder 210. Spring 211 returns to its uncompressed condition and lancet holder 210 is projected downwardly in housing 215 until it abuts against stop 222 which is formed in the housing. During this motion lift-pin 212 is sheared off by sharp edge 217 of the slot. Thus, the invention cannot be reloaded and inadvertent reuse is prevented; this feature further contributes to the disposable nature of the invention. When lancet holder 210 contacts stop 222, retraction spring 213 becomes compressed and lancet 214 passes through aperture 219 to penetrate the patient's skin. The travel of the lancet holder is limited by the position of stop 222. This effectively controls the depth of penetration of the patient's skin by the lancet.

Figure 27:
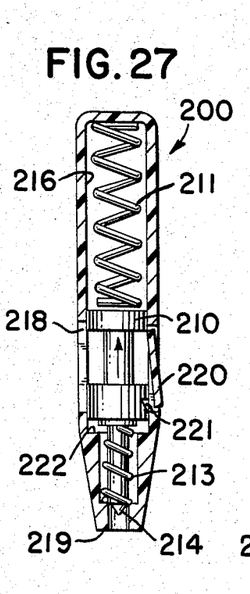
FIG. 27 is a cross-sectional view of the lancet assembly of FIG. 23 illustrating the lancet retracted back inside the assembly.
Figure 28:
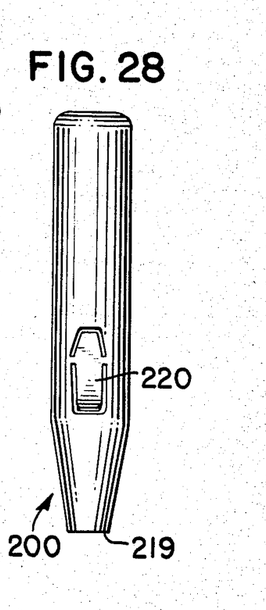
FIG. 28 is an opposite side view of the lancet assembly of FIG. 23.

In FIG. 27, the assembly is illustrated immediately following the retraction of lancet 214 inside the housing. Retraction spring 213 has extended and lancet holder 210 has been withdrawn. Retraction spring 213 is preferably a light spring because the lance holder is completely dissociated from the main spring following the extension or return to normal state of main spring 211. Therefore, the retraction spring serves only to withdraw the unrestrained lancet holder, as in the previously described embodiments.

Thus, there has been provided in accordance with the present invention an automatic retractable lancet assembly. While two springs are preferably employed, the return spring operates independently and is dissociated from any movement of the driving spring. Accordingly, balance of spring forces is not required as in prior art lancet assemblies. This allows more straightforward operation, reduction of spring sizes and lighter weight materials.

What is claimed is:

1. An automatic retractable lancet assembly comprising:
   a housing having an aperture;
   a lancet movably mounted in said housing with its point lying substantially adjacent the interior side of said aperture;
   a first spring mounted inside said housing in a substantially relaxed condition adapted to be compressed in a biased condition and further adapted to decompress upon release to cause the movement of said lancet outward of said aperture for penetration of the skin of a patient, said first spring adapted to become dissociated from further movement of said lancet after said lancet completes its outward movement;
   actuating means for compressing said first spring into a biased condition and for retaining same until use, and for releasing same to cause the outward movement of said lancet;
   said actuating means including a slidable member through said housing associated with said first spring and including a latching means so that said first spring is compressible by movement of said slidable member and is retained in position by co-operation with said latching means;
   said slidable member being adapted to be forcibly removed from said assembly upon decompression of said first spring so that said first spring cannot be reloaded for a subsequent operation; and
   a second spring mounted inside said housing in a substantially relaxed condition before said first spring is released and adapted to become biased when said first spring becomes dissociated from further movement of said lancet to cause said lancet to be automatically retracted back inside said housing.

2. The assembly of claim 1 wherein said actuating means includes a depressible button on said housing adapted to retain said first spring in a compressed condition and to release said first spring from its compressed condition when depressed.

* * * * *